(12) United States Patent
Wilson et al.

(10) Patent No.: US 6,399,837 B1
(45) Date of Patent: Jun. 4, 2002

(54) ELECTRON DONORS

(75) Inventors: Stanley Edward Wilson; Robert Converse Brady, III, both of Houston, TX (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/589,869

(22) Filed: Jun. 5, 2000

Related U.S. Application Data

(63) Continuation-in-part of application No. 08/988,227, filed on Dec. 10, 1997, now Pat. No. 6,124,507.

(51) Int. Cl.[7] .............................................. C07C 43/263
(52) U.S. Cl. ...................... 568/648; 568/630; 568/656; 568/657; 526/125; 502/118; 502/126
(58) Field of Search ................................ 568/648, 630, 568/656, 657; 502/126, 118; 526/125

(56) References Cited

U.S. PATENT DOCUMENTS

| | | |
|---|---|---|
| 3,764,629 A | 10/1973 | Gurien et al. |
| 4,107,413 A | 8/1978 | Giannini et al. |
| 4,107,414 A | 8/1978 | Giannini et al. |
| 4,393,182 A | 7/1983 | Goodall et al. |
| 4,680,054 A | 7/1987 | Takematsu et al. |
| 4,710,482 A | 12/1987 | Job |
| 4,971,936 A | 11/1990 | Wilson et al. |
| 4,988,730 A | 1/1991 | Korbonits et al. |
| 5,077,357 A | 12/1991 | Job |
| 5,093,415 A | 3/1992 | Brady, III et al. |
| 5,352,570 A | 10/1994 | Begley |
| 5,968,865 A | 10/1999 | Wilson et al. |

FOREIGN PATENT DOCUMENTS

| | | | |
|---|---|---|---|
| BE | 831230 | 9/1976 | |
| DE | 3633131 | 3/1988 | |
| EP | 134576 | 3/1985 | |
| GB | 898045 | 3/1962 | |
| JP | 49/048638 | 2/1974 | |
| JP | 61002727 | * | 1/1986 |
| JP | 01/297408 | 11/1989 | |
| JP | 6/23278 | 2/1994 | |
| JP | 2613169 | 5/1997 | |

OTHER PUBLICATIONS

Akazome et al, Bull.Chem.Soc.Jpn., 70(11),2823–2827 (1997).*
Sheu et al, JACS, 118(34), 8056–8070 (1996).*
Khrimian et al, J.Chem.Ecol., 19(12), 2935–46 (1993).*
Kajigaeshi et al, Chem.Lett., (3), 415–418 (1989).*
Hynning et al, J.Chromatog., 467(1), 99–110 (1989).*
Sauer et al, Mol.Cryst.liq.Cryst., 162B, 97–118 (1988).*
James et al, J.Fluorine Chem., 27(1), 91–104 (1985).*

* cited by examiner

Primary Examiner—Sreeni Padmanabhan

(57) ABSTRACT

A method of polymerizing at least one olefin comprising contacting the olefin with a catalyst composition comprising:

1) a procatalyst composition comprising a magnesium and titanium-containing component and an electron donor compound of the structure:

(I)

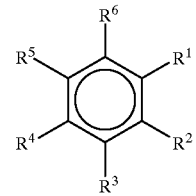

wherein $R^1$ is ethoxy, and $R^2$ is an alkoxy group having from one to ten carbon atoms, and $R^3$–$R^6$ are each individually, hydrogen, hydrocarbyl, hydrocarboxy, nitro, a silyl group or a halogen, 2) a cocatalyst and optionally 3) a selectivity control agent.

13 Claims, 3 Drawing Sheets

ELECTRON DONORS

RELATED APPLICATION

This application is a continuation-in-part of application Ser. No. 08/988,227, filed on Dec. 10, 1997 now U.S. Pat. No. 6,124,507 and entitled: "Novel Electron Donors," the disclosure of which is incorporated by reference herein in its entirety.

BACKGROUND OF THE INVENTION

1. Field of the Invention

Embodiments of the present invention relate to 1-ethoxy-2-n-alkoxybenzene compounds, and particularly to their use as internal electron donors in catalysts useful for polymerizing olefins. The compounds of the invention provide high activity catalysts.

2. Description of Related Art

Ziegler-Natta catalysts are used to polymerize olefins. These catalysts contain a procatalyst made from an internal electron donor, a titanium source, a magnesium source and a halogenating agent (which may be combined with one of the other components). The use of these catalysts is known where this procatalyst is combined with an external electron donor or more commonly called a selectivity control agent ("SCA") and a cocatalyst. See, e.g., U.S. Pat. No. 5,093,415 to Brady et al.

One class of electron donors taught by the art is veratrole (1,2-dimethoxybenzene) and certain derivatives thereof which incorporate additional substituents on the benzene ring. See, e.g., U.S. Pat. No. 4,971,936 to Wilson et al. See also U.S. Pat. No. 4,107,413 to Giannini et al. However, these specific compounds have certain deficiencies in that catalysts made with them have low catalytic activity (<20 kg polymer/procatalyst per hour) and produce polymers of low crystallinity (e.g., isotactic polypropylene with a xylene soluble content of greater than 30% wt and a $L_{(iso)}$ ($^1$H NMR) of less than 50 even with a SCA). The use of these electron donor compounds solely to produce polymers of low crystallinity is confirmed in Japanese patent application Nos. 2613169 and H1-307519. It is desirable to find electron donors which result in catalysts of improved activity and selectivity.

SUMMARY OF INVENTION

The novel electron donors (hereinafter "ED") of the present invention are of the formula

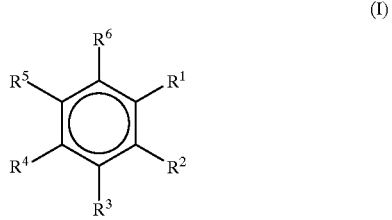

(I)

wherein $R^1$ is an ethoxy group, and $R^2$ is an alkoxy group, having from one to ten carbon atoms, and $R^3$–$R^6$ are each individually, hydrogen, a hydrocarbyl group, a hydrocarboxyl group, a silyl group, a nitro group, or a halogen. These EDs are used in the manufacture of olefin polymerization catalysts with procatalysts having magnesium, titanium and halide as essential components.

DETAILED DESCRIPTION OF THE INVENTION

Figure 1:
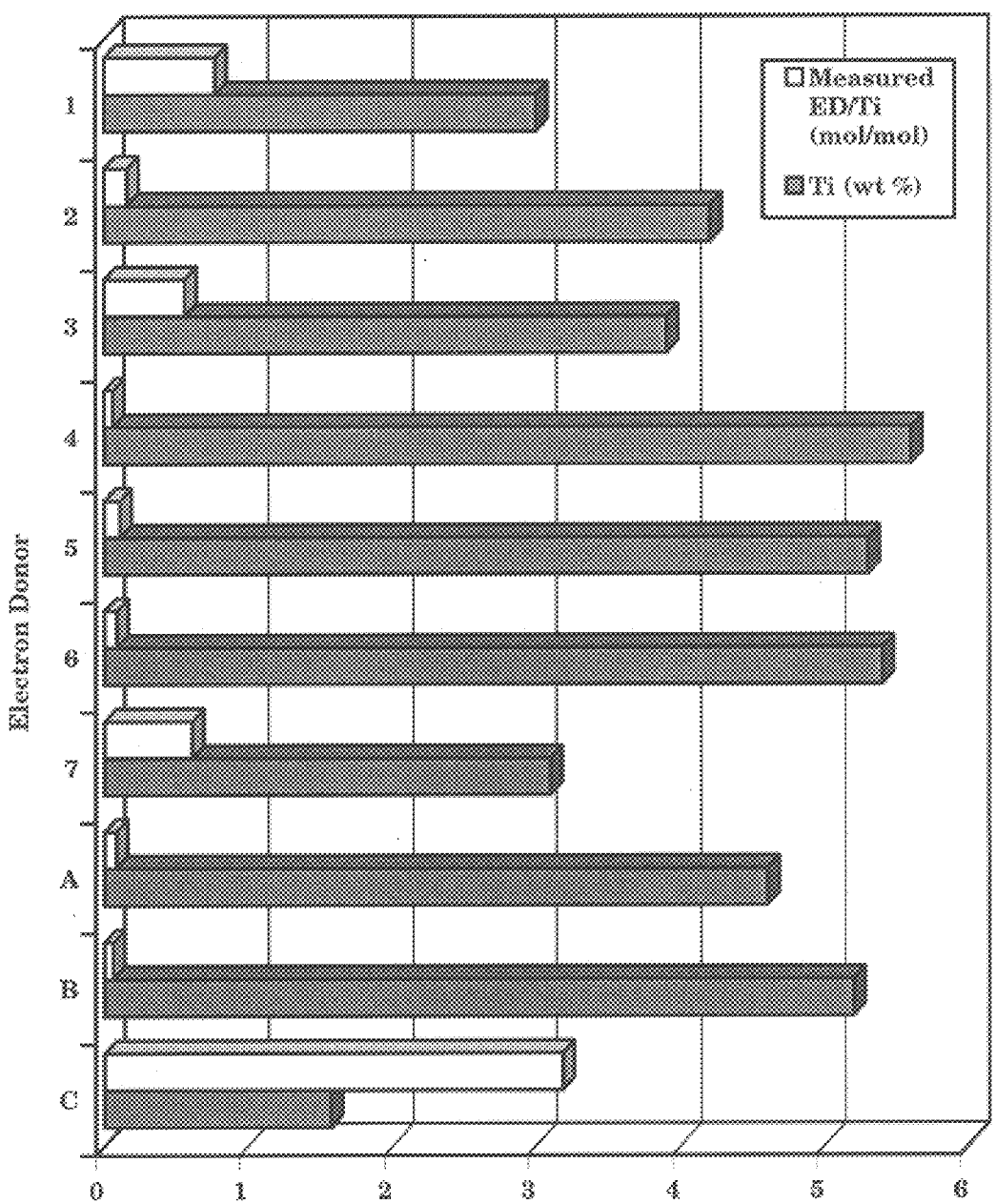
FIG. 1 is a plot of the composition of various electron donor containing procatalysts.

The electron donor of the present invention preferably is of the Formula I above wherein $R^1$ is ethoxy and $R^2$ is an alkoxy groups of $C_1$–$C_{10}$, which may be linear, branched or cyclic, $R^3$–$R^6$ are hydrogen, hydrocarbyl, hydrocarboxyl, nitro group, silyl or a halogen. Preferably, $R^2$ is an alkoxy group of $C_2$–$C_{10}$, more preferably $C_2$–$C_6$. $R^2$ may be branched; however, when the branching of the alkoxy functionalities ($R^2$) is at the carbon attached to the oxygen atom, the electron donor is not loyal to the surface of the catalyst precursor and the resulting catalyst is not rewarded with enhanced productivity and the preservation of selectivity. Therefore, it is preferred to have the steric bulk created by branching at least one carbon away from the oxygen atom (e.g., isopentoxy). Specific alkoxy groups for $R^2$ are propoxy, n-propoxy, n-butoxy, neo-pentoxy, n-pentoxy, isopentoxy, neo-hexoxy, n-hexoxy, n-heptoxy, n-octoxy, 3-phenylpropoxy, 3-cyclohexylpropoxy, and 4-cyclopentylbutoxy. Particularly preferred alkoxy groups for $R^2$ are n-propoxy, n-butoxy, n-pentoxy, n-hexoxy, and n-octoxy.

The $R^3$–$R^6$ groups each individually may be hydrogen, hydrocarbyl, [e.g., an alkyl (e.g., methyl or t-butyl), cycloaliphatic (e.g., cyclopentyl), aryl (e.g., naphthyl or alkaryl)], hydrocarboxy (e.g., an alkoxy, aryloxy or aralkoxy), silyl (e.g., triethylsilyl or trimethyl silyl), nitro, or a halogen (e.g., Cl or F). If $R^3$–$R^6$ are hydrocarbyl or hydrocarboxy, preferably it has from one to ten carbon atoms. Preferably, only one or none of $R^3$ to $R^6$ are groups other than hydrogen. If substitution occurs on the benzene ring other than in the $R^1$ and $R^2$ position, it preferably is at the $R^4$ position.

Specifically preferred EDs include, but are not limited to, 1-ethoxy-2-methoxy-4-methylbenzene; 1-ethoxy-2-n-propoxybenzene; 1-ethoxy-2-n-butoxybenzene; 1-ethoxy-2-n-pentoxybenzene; 1-ethoxy-2-isopentoxybenzene; 1-ethoxy-2-n-hexoxybenzene; 1-ethoxy-2-n-octoxybenzene, 1-ethoxy-2-(3-phenylpropoxy)benzene, 1-ethoxy-2-(3-cyclohexylpropoxy)benzene, and 1-ethoxy-2-(4-cyclopentylbutoxy)benzene. The preferable ED is selected from 1-ethoxy-2-n-propoxybenzene; 1-ethoxy-2-n-butoxybenzene; 1-ethoxy-2-n-pentoxybenzene; 1-ethoxy-2-n-hexoxybenzene; 1-ethoxy-2-n-octoxybenzene, and 1-ethoxy-2-(3-phenylpropoxy)benzene.

A. Electron Donor Manufacture

The ED may be manufactured using 2-alkoxy phenol (e.g., 2-ethoxy phenol), which is commercially available, as a starting material. This is combined with an alkyl halide of the desired alkoxy substituent, e.g., 1-iodopropane in the presence of a base. Preferred alkyl halides include, but are not limited to, 1-iodopropane, 1-bromopropane, 1-chloropropane, 1-bromobutane, 1-bromo-3-methylbutane, 1-bromopentane, 1-bromohexane, and 1-bromooctane. Such substitution by salt elimination reactions are known in the art. The benzene ring may be substituted at the 3–6 positions using the alcohol of the substituent in an acid catalyzed reaction in solvent at elevated temperature.

The solvent for this reaction is preferably water. Separation from water may be by phase separation techniques known in the art, e.g., solvent extraction.

These EDs may be used either as the internal ED, the SCA or as both.

B. Procatalyst

The procatalysts preferably contain a magnesium and titanium-containing component, together with the above-described ED. More preferable, the procatalysts include magnesium, titanium, and a halogen, along with either the above-described ED or an ED known in the art, said procatalyst being used to form a catalyst for the polymerization of olefins. The halide is introduced into the procatalyst with either the magnesium or titanium source.

i. Magnesium

The magnesium source preferably is in the form of a procatalyst precursor prepared in accordance with any of the procedures described in, for example, U.S. Pat. Nos. 5,034,361; 5,082,907; 5,151,399; 5,229,342; 5,106,806; 5,146,028; 5,066,737; and 5,077,357, the disclosures of which are incorporated by reference herein in their entirety. The magnesium source also may be a magnesium halide, alkyl, aryl, alkaryl, alkoxide, alkaryloxide or aryloxide, alcohol adducts thereof or carbonated derivatives thereof, but preferably is a magnesium dialkoxide, carbonated magnesium dialkoxide, or a carbonated magnesium diaryloxide. Magnesium compounds containing one alkoxide and one aryloxide group can also be employed, as well as magnesium compounds containing a halogen in addition to one alkoxide, alkaryloxide or aryloxide group. The alkoxide groups, when present, most suitably contain from 1 to 8 carbon atoms, preferably from 2 to 6 carbon atoms. The aryloxide groups when present, most suitably contain from 6 to 10 carbon atoms. When halogen is present, it is preferably chlorine.

Among the magnesium dialkoxides and diaryloxides which can be employed are those of the formula $Mg(O(C(O)OR')_x(OR'')_{2-x}$, wherein R' and R' are alkyl, alkaryl or aryl groups, and x is about 0.1 to about 2. The most preferable magnesium compound is carbonated magnesium diethoxide (CMEO),

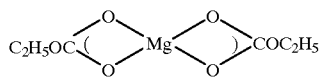

Optionally, the magnesium may be halogenated with an additional halogenating agent, e.g., thionyl chloride or alkylchlorosilanes, prior to its contact with the tetravalent titanium source.

A somewhat different type of magnesium source is described by the general formula

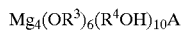

(I)

in which each $R^3$ or $R^4$ is a lower alkyl of up to 4 carbon atoms inclusive and A is one or more anions having a total charge of −2. The manufacture of this magnesium source is disclosed in U.S. Pat. No. 4,710,482 to Job which is incorporated herein by reference.

Another particularly preferred magnesium source is one that contains moieties of magnesium and titanium and probably moieties of at least some of halide, alkoxide and a phenolic compound. Such complex procatalyst precursors are produced by contacting a magnesium alkoxide, a titanium alkoxide, a titanium halide, a phenolic compound and an alkanol. See U.S. Pat. No. 5,077,357 to Job, which is incorporated herein by reference.

ii. Titanium

The titanium source for the procatalyst preferably is a tetravalent titanium which contains at least two halogen atoms, and preferably contains four halogen atoms, e.g., $Ti(OR^5)_nX_{4-n}$, wherein $R^5$ is a hydrocarbon, and X is a halide and n is 0 to 2. Most preferably these halogen atoms are chlorine atoms. Titanium compounds containing up to two alkoxy, alkaryloxy or aryloxy groups can be employed. The alkoxy groups, when present, most suitably contain from 1 to 8 carbon atoms, preferably 2 to 6 carbon atoms. The aryloxy or alkaryloxy groups, when present, most suitably contain from 6 to 12 carbon atoms, preferably from 6 to 10 carbon atoms. Examples of suitable alkoxy- and aryloxy-titanium halides include diethoxy titanium dibromide, isopropoxy titanium triiodide, dihexoxy titanium dichloride, and phenoxy titanium trichloride. The most preferable titanium source is $TiCl_4$.

iii. Standard EDs

If the ED of the present invention is used as an external selectivity control agent ("SCA"), other EDs may be used as the internal ED, which may be those EDs free from active hydrogens which are conventionally employed in the formation of titanium-based procatalysts. Such EDs include ethers, esters, amines, imines, nitriles, phosphines, stibines, and arsines. The preferred EDs are esters, particularly alkyl esters of aromatic monocarboxylic or dicarboxylic acids. Examples of such EDs are methyl benzoate, ethyl benzoate, ethyl p-ethoxybenzoate, ethyl p-ethylbenzoate, diethyl phthalate, dimethyl naphthalene dicarboxylate, diisobutyl phthalate (DIBP) and diisopropyl terephthalate. The ED is a single compound or is a mixture of compounds but preferably the ED is a single compound. Of the preferred ester EDs, ethyl benzoate (EB) and DIBP are particularly preferred if a standard ED is used.

iv. Procatalyst Manufacture

The magnesium compound preferably is reacted (i.e., halogenated) with the tetravalent titanium halide in the presence of an ED and preferably a halohydrocarbon. Optionally, an inert hydrocarbon diluent or solvent also may be present.

The halohydrocarbon employed may be aromatic, aliphatic, or alicyclic. Most preferably, the halogen of the halohydrocarbon is chlorine. Aromatic halohydrocarbons are preferred, particularly those containing from 6 to 12 carbon atoms, preferably 6 to 10 carbon atoms. Preferably such halohydrocarbons contain 1 or 2 halogen atoms, although more may be present if desired. Suitable aromatic halohydrocarbons include, but are not limited to chlorobenzene, bromobenzene, dichlorobenzene, dichlorodibromobenzene, chlorotoluene, dichlorotoluene, and chloronaphthalene. The aliphatic halohydrocarbons contain from 1 to 12 carbon atoms, preferably from 1 to 9 carbon atoms and at least 2 halogen atoms. Suitable aliphatic halohydrocarbons include, but are not limited to dibromomethane, trichloromethane, 1,2-dichloroethane, trichloroethane, dichlorofluoroethane, hexachloroethane, trichloropropane, chlorobutane, dichlorobutane, chloropentane, trichlorofluorooctane, tetrachloroisooctane, dibromodifluorodecane, carbon tetrachloride, and trichloroethane. The alicyclic halohydrocarbons which can be employed contain from 3 to 12 carbon atoms, and preferably from 3 to 9 carbon atoms, and at least 2 halogen atoms. Suitable alicyclic halohydrocarbons include dibromocyclobutane, and trichlorocyclohexane.

The optional inert hydrocarbon diluent may be aliphatic, aromatic or alicyclic. Some exemplary diluents are isopentane, n-octane, isooctane, xylene, or toluene.

Halogenation of the magnesium compound with the halogenated tetravalent titanium halide is effected employing an excess of the titanium halide. At least 2 moles of the titanium halide should be employed per mole of the magnesium compound. Preferably from about 4 moles to about 100 moles of the titanium halide are employed per mole of the magnesium compound, and most preferably from about 4 moles to about 20 moles of the titanium halide are employed per mole of the magnesium compound.

The halohydrocarbon is employed in an amount sufficient to dissolve the titanium halide and the ED, and to adequately disperse the magnesium compound. Usually the dispersion contains from about 0.005 to about 2.0 moles of the solid magnesium compound per mole of halohydrocarbon, preferably from about 0.01 to about 1.0 mole of the solid magnesium compound per mole of the halohydrocarbon. The ED is employed in an amount sufficient to provide a molar ratio of said compound to the titanium halide of from about 0.0005:1 to about 2.0:1, preferably from about 0.001:1 to about 0.1:1. 1:100 to 100:1 by volume of halohydrocarbon to diluent may be used.

Halogenation can be effected at a temperature of from about 60° C. to about 150° C., preferably from about 90° C. to about 140° C. Generally, as the temperature is increased the ED content drops while the titanium loading rises. Usually the reaction is allowed to proceed over a period of 0.1 to 6 hours, preferably between about 0.5 to about 3.5 hours. For convenience, halogenation is usually effected at atmospheric pressure, although a range of pressures can be employed, e.g., 0.5 atm (50,700 Pa) to 5 atm (507,000 Pa). The halogenated product, like the starting magnesium compound, is a solid material which can be isolated from the liquid reaction medium by drying, filtration, decantation, evaporation, distillation or any suitable method.

After separation, the halogenated product may be treated one or more times with additional tetravalent titanium halide to remove residual alkoxy and/or aryloxy groups and maximize catalyst activity or other desired properties. Preferably, the halogenated product is treated at least twice with separate portions of the tetravalent titanium halide. Generally, the reaction conditions employed to treat the halogenated product with the titanium halide are the same as those employed during the initial halogenation of the magnesium compound, and the ED may or may not be present during this treatment, though it is preferred that it be present. The halohydrocarbon usually is employed to dissolve the titanium halide and disperse the solid, halogenated product. If desired, the halogenated product may be treated with the acid halide before or after it is treated with the titanium compound for the second time. From 5 mmol to 200 mmol of the acid halide generally are employed per gram atom of magnesium of the halogenated product. Suitable acid halides include benzoyl chloride, phthaloyl dichloride, 2,3-naphthalenedicarboxylic acid dichloride, endo-5-norbornene-2,3-dicarboxylic acid dichloride, maleic acid dichloride, citraconic acid dichloride, and the like.

After the solid halogenated product has been treated one or more times with additional tetravalent titanium halide, it is separated from the liquid reaction medium, washed with an inert hydrocarbon to remove unreacted titanium compounds, and dried. Drying may be by filtration, evaporation, heating or other methods known in the art.

The final washed procatalyst product suitably has a titanium content of from about 0.5 percent by weight to about 6.0 percent by weight, preferably from about 1.5 percent by weight to about 4.0 percent by weight. The atomic ratio of titanium to magnesium in the final procatalyst product is suitably between about 0.01:1 and about 0.2:1, preferably between about 0.02:1 and about 0.1:1. The ED is present in the procatalyst in a ratio of ED to magnesium of from about 0.001:1 to about 10.0:1, preferably from about 0.02:1 to about 2.0:1.

C. Catalyst

The olefin polymerization catalyst includes the above-described procatalyst, a cocatalyst and a selectivity control agent ("SCA").

i. Cocatalyst

The cocatalyst may be chosen from any of the known activators of olefin polymerization catalyst systems, but organoaluminum compounds are preferred. Such cocatalysts can be employed individually or in combinations thereof. Suitable organoaluminum cocatalysts have the formula $Al(R''')_d X_e H_f$ wherein: X is F, Cl, Br, I or OR'''', R''' are saturated hydrocarbon radicals containing from 1 to 14 carbon atoms, which radicals may be the same or different, and, if desired, substituted with any substituent which is inert under the reaction conditions employed during polymerization, d is 1 to 3, e is 0 to 2, f is 0 or 1, and d+e+f=3. Trialkylaluminum compounds are particularly preferred, particularly those wherein each of the alkyl groups contains from 1 to 6 carbon atoms, e.g., $Al(CH_3)_3$, $Al(C_2H_5)_3$, $Al(i-C_4H_9)_3$, and $Al(C_6H_{13})_3$.

ii. SCA

The SCA is either the ED of Structure I or one of those known in the art. The SCA is the electron donor of Structure I, if the ED is not of Structure I. The SCAs known in the art include, but are not limited to, silicon compounds, esters of carboxylic acids, (especially diesters), monoethers, diethers (e.g., 1,3 dimethoxy propane or 2,2 diisobutyl-1,3 dimethoxy propane), and amines (e.g., tetramethyl piperdine).

Preferably, the silicon compounds employed as SCAs contain at least one silicon-oxygen-carbon linkage. Suitable silicon compounds include those having the formula $R^1_m SiY_n X_p$ wherein: $R^1$ is a hydrocarbon radical containing from 1 to 20 carbon atoms, Y is $—OR^2$ or $—OCOR^2$ wherein $R^2$ is a hydrocarbon radical containing from 1 to 20 carbon atoms, X is hydrogen or halogen, m is an integer having a value of from 0 to 3, n is an integer having a value of from 1 to 4, p is an integer having a value of from 0 to 1, and preferably 0, and m+n+p=4. Preferably, $R^1$ and $R^2$ are alkyl, aryl or alkaryl ligands of $C_1$–$C_{10}$. Each $R^1$ and $R^2$ may be the same or different, and, if desired, substituted with any substituent which is inert under the reaction conditions employed during polymerization. Preferably, $R^2$ contains from 1 to 10 carbon atoms when it is aliphatic and may be sterically hindered or cycloaliphatic, and from 6 to 10 carbon atoms when it is aromatic.

Examples of $R^1$ include cyclopentyl, t-butyl, isopropyl, cyclohexyl or methyl cyclohexyl. Examples of $R^2$ include methyl, ethyl, butyl, isopropyl, phenyl, benzyl and t-butyl. Examples of X are Cl and H. Preferred silicon SCAs are alkylalkoxysilanes such as diethyldiethoxysilane, diphenyl dimethoxy silane, diisobutyldimethoxysilane, cyclohexylmethyldimethoxysilane, n-propyltrimethoxysilane or dicyclopentyl dimethoxysilane.

Silicon compounds in which two or more silicon atoms are linked to each other by an oxygen atom, i.e., siloxanes or polysiloxanes, may also be employed, provided the requisite silicon-oxygen-carbon linkage is also present. Other preferred SCAs are esters of aromatic monocarboxylic or dicarboxylic acids, particularly alkyl esters, such as PEEB, DIBP, and methyl paratoluate.

In one modification, the SCA is a portion of the ED added during the procatalyst production if multiple electron donors are used or both SCA and ED may be of Structure I. In an alternate modification the SCA is provided at the time of the contacting of procatalyst and cocatalyst.

The SCA is provided in a quantity sufficient to provide from about 0.01 mole to about 100 moles per mole of titanium in the procatalyst. It is preferred that the SCA is provided in a quantity sufficient to provide from about 0.5 mole to about 70 moles per mole of titanium in the procatalyst, with about 8 moles to about 50 moles being more preferred. Mixtures of two or more SCA's may be used.

The components of the olefin polymerization catalyst can be contacted by mixing in a suitable reactor outside the system in which olefin is to be polymerized and the catalyst thereby produced subsequently is introduced into the polymerization reactor. The premixed components may be dried after contact or left in the contact solvent. Alternatively, however, the catalyst components may be introduced separately into the polymerization reactor. As another alternative, two of the components may be mixed partially or completely with each other (e.g. premixing SCA and cocatalyst) prior to being introduced into the polymerization reactor. Another alternative is to contact the procatalyst with an aluminum alkyl halide prior to reaction with the other catalyst components. A different alternative is to pre-polymerize a small amount of olefin with the catalyst components or put any of the components on a support, e.g., silica or a non-reactive polymer.

The catalyst should have an activity of at least about 25 kg polymer per gram procatalyst per hour, preferably at least about 35 kg polymer per gram procatalyst per hour.

D. Polymerization

The olefin polymerization catalyst is useful in the (co) polymerization of olefins of up to 20 carbon atoms, inclusive, e.g., ethylene, propylene, 1-butene, 1-dodecene, 1,3-butadiene, 7-methyl-1,6-octadiene, or mixtures thereof, are contemplated herein as well. It is preferred that alpha-olefins of 3 carbon atoms to 10 carbon atoms, such as propylene, butene-1 and pentene-1 and hexene-1, are homopolymerized, though copolymers, such as $C_2/C_3$ and $C_3/C_4$ copolymers, and terpolymers may also be produced. Moreover, multi-stage polymers may be produced with the catalyst of the present invention, e.g., an impact copolymer including a propylene homopolymer phase with an ethylene-propylene rubber phase.

The invention is useful for the production of isotactic, crystalline polypropylene (iPP) and other stereospecific polymerizations. Preferably, the xylene solubles content (XS) of iPP as measured according to 21 CFR 177.1520 is less than fifteen (15) percent by weight, more preferably, less than eight (8) weight percent of the polymer and even more preferably less than five weight percent of the polymer. Moreover, for iPP the $L_{(iso)}$ as measured by $^1$H NMR is greater than 30, more preferably greater than 50, most preferably greater than 70.

The polymerization is conducted under polymerization conditions in a liquid phase, slurry phase or a gas-phase process employing a stirred or fluidized bed. In both the liquid phase and the gas-phase polymerization processes, molecular hydrogen is added to the reaction mixture as a chain transfer agent to regulate the molecular weight of the polymeric product.

EXAMPLES 1–7 AND COMPARATIVE EXAMPLES A–C

The following abbreviations are used in the examples.

| Abbreviation | Meaning |
| --- | --- |
| MT | A magnesium source produced as described in U.S. Pat. No. 5,077,357 |
| DCPDMS | dicyclopentyldimethoxysilane (SCA) |
| TEAL | triethylaluminum (cocatalyst) |
| MCB | monochlorobenzene |
| MF | melt flow of polymer measured in accordance with ASTM D-1238, Condition L. |
| XS | xylene solubles content (wt %) (21 CFR 177.1520) |

ED Synthesis

This synthesis of 1-ethoxy-2-isopentoxybenzene is representative of the synthesis of the non-commercially available EDs via substitution reactions by salt elimination. 200 mmol of 2-ethoxyphenol was added to a stirring solution of 417 mmol of sodium hydroxide in 90 ml of water. Following the addition of 400 mmol of 1-bromo-3-methylbutane, the mixture was refluxed for 6 hours. The two phase liquid was extracted with hexanes. The organic phase was washed with a sodium hydroxide solution followed by a sodium chloride solution. The organic phase was then dried over magnesium sulfate and distilled. A 38% yield was obtained of the 1-ethoxy-2-isopentoxybenzene product as determined by $^1$H NMR.

Procatalyst Preparation 3.0 g of MT containing 12% Mg was slurried in a volume of 60 ml of a 50/50 by (vol/vol) mixture of $TiCl_4$/MCB with an ED for 60 minutes at a temperature ranging from 110 to 130° C. The resulting mixture was filtered while hot. The recovered solids were slurried in 60 ml of the fresh 50/50 mixture and ED for 60 minutes at the same temperature used in the first step. The resulting mixture was filtered while hot. The recovered solids were slurried again in 60 ml of the fresh 50/50 mixture and ED for 60 minutes at the same temperature used in the first step. The resulting mixture was filtered while hot and the solids recovered. The solids were rinsed three times with 70 ml of isooctane at room temperature, and then dried for at least two hours under flowing nitrogen. Typical recovery of the precursor was approximately 2 g. The volume of ED added to each step, the temperature, and analysis of these procatalyst preparations are shown in Table 1. A comparative example (C) of a precursor made with veratrole as the internal ED had a lower Ti content and a higher ED/Ti ratio than the EDs of the present invention. FIG. 1 is a plot of the ED versus the procatalyst properties of ED/Ti mole ratio and Ti weight percent.

Figure 2:
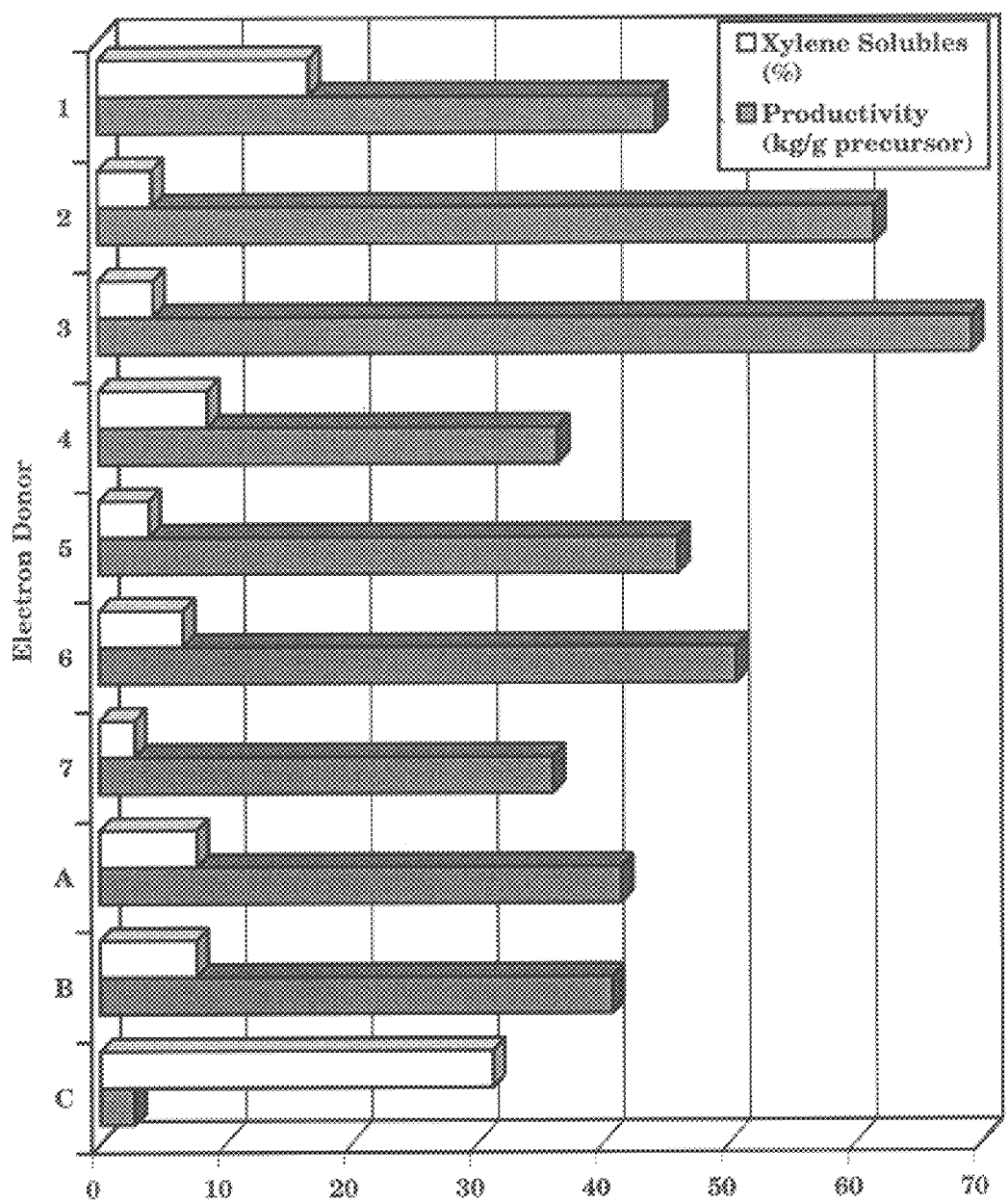
FIG. 2 is a plot of catalyst productivity and for catalysts containing certain electron donors (productivity and xylene solubles content for polymers produced from said catalysts.

Liquid Propylene Stirred Polymerization Procedure 2.7 l of liquid propylene was added to a cooled 1-gallon autoclave that had been dried under a stream of nitrogen at greater than 90° C. To the stirred autoclave at 62° C. were added 1.5 l of hydrogen, 58 μl of DCPDMS (0.24 mmol), 3.6 ml of 5.0% by weight TEAL solution in heptane (1.0 mmol), and from 11 to 17 mg of procatalyst as a 5% by weight mineral oil slurry. The polymerization took place for 60 minutes at 67° C. The results of these polymerizations are shown in the Table wherein "Productivity" refers to the yield of polypropylene polymer in kg of polymer/g procatalyst per hour. A comparative example (C) of polymerization with a catalyst made with veratrole as the internal ED had a much lower productivity and much higher XS than catalysts made with EDs of the present invention. FIG. 2 is a plot of ED versus the catalyst productivity and XS of polymer produced by the catalyst.

was labeled example 10, and the structure was confirmed by NMR spectroscopy.

TABLE I

| Example | Electron Donor | ED (ml) | Prep Temp (° C.) | Ti (wt %) | Measured ED/Ti (mol/mol) | Productivity (kg/g precursor) | Xylene Solubles (%) |
|---|---|---|---|---|---|---|---|
| 1 | 1-Ethoxy-2-methoxybenzene | 0.05 | 110 | 3.0 | 0.77 | 44.3 | 16.8 |
| 2 | 1-Ethoxy-2-isopentoxybenzene | 1.4 | 130 | 4.2 | 0.16 | 61.6 | 4.3 |
| 3 | 1,2-Diethoxybenzene | 1.2 | 130 | 3.9 | 0.56 | 69.3 | 4.4 |
| 4 | 1,2-Diethoxy-3-methylbenzene | 1.5 | 110 | 5.6 | 0.06 | 36.4 | 8.7 |
| 5 | 1,2-Diethoxy-3-fluorobenzene | 1.2 | 130 | 5.3 | 0.11 | 46.0 | 4.0 |
| 6 | 1,2-Diethoxy-3-(trimethylsilyl)benzene | 0.7 | 130 | 5.4 | 0.09 | 50.6 | 6.7 |
| 7 | 1,2-Diethoxy-4-t-butylbenzene | 1.5 | 130 | 3.1 | 0.61 | 36.0 | 2.8 |
| A | 1,2-Di-n-propoxybenzene | 1.2 | 130 | 4.6 | 0.08 | 41.4 | 7.7 |
| B | 1,2-Di-n-butoxybenzene | 1.6 | 130 | 5.2 | 0.06 | 40.7 | 7.7 |
| C | Veratrole | 1.0 | 130 | 1.6 | 3.18 | 2.7 | 31.2 |

EXAMPLES 8–13

Electron Donor Synthesis

The synthesis of six 1-ethoxy-2-n-alkoxybenzenes was accomplished in a one-step fashion as described above in Examples 1–7.

1-Ethoxy-2-n-propoxybenzene (I)

The reaction was conducted in a 500-ml 3-neck flask equipped with a reflux condenser, an addition funnel, and a magnetic stirring bar. Into the flask was introduced 75 ml water, 11.5 grams of 50% aqueous sodium hydroxide, 19.3 grams (0.14 moles) 2-ethoxyphenol, and 23.8 grams (0.14 moles) 1-iodopropane. The flask contents were maintained at 80° C. for a period of 7 hours and were then cooled to room temperature. After the addition of 100 ml of water the reaction mixture was transferred to a 250-ml separatory funnel and washed twice with 100-ml quantities of hexane. The organic layer was washed twice with 10 ml of 15% aqueous sodium hydroxide and dried over anhydrous magnesium sulfate. Most of the solvent was removed by simple distillation. A liquid was isolated which boiled at 63–67° C. @ 0.05 mm. It was labeled example 8, and the structure confirmed by glpc and NMR analysis.

1-Ethoxy-2-n-butoxybenzene (II)

The procedure was similar to that followed in the preparation of example 8 above, except that the reaction involved 150 ml of water, 15.8 ml of 50% sodium hydroxide solution, 25.4 ml (0.2 moles) of 2-ethoxyphenol, and 21.5 ml (0.2 moles) of 1-bromobutane. This compound was labeled as example 9.

1-Ethoxy-2-n-pentoxybenzene (III)

The procedure was similar to that followed in the preparation of example 9 above. A liquid product distilled at 86–98° C. @ 0.05 mm and weighed 33.1 grams. The product 1-Ethoxy-2-n-hexoxybenzene (IV)

The procedure was similar to that followed in the preparation of example 9 above. A liquid product distilled at 110–115° C. @ 0.05 mm and weighed 27.6 grams. The product was labeled example 11 and the structure was confirmed by NMR spectroscopy.

1-Ethoxy-2-n-heptoxybenzene (IV)

The procedure was similar to that followed in the preparation of example 9 above. The product was labeled example 12 and the structure was confirmed by NMR spectroscopy.

1-Ethoxy-2-n-octoxybenzene (VI)

The procedure was similar to that followed in the preparation of example 9 above. A liquid product distilled at 126–128° C. @ 0.05 mm and weighed 15.1 grams. The product was labeled example 13, and the structure was confirmed by NMR spectroscopy.

Procatalysts were prepared using each of the above examples 8–13 in accordance with the procedures outlined above with respect to examples 1–7. The procatalyst preparations usually involved addition of the 1-ethoxy, 2-n-alkoxybenzene to each hot mixed solvent contact, digest, A1, and A2. Also, in most cases the temperature of each mixed solvent contact for a given preparation was held constant. The following table 2 summarizes the analyses of the 1-ethoxy-2-n-alkoxybenzene compounds prepared above. The items of interest were titanium, ethoxide (OEt), and incorporation of electron donor under a variety of preparation conditions.

TABLE 2

| Example | Digest Temp | A1 Temp | A2 Temp | ENAB in Digest (ml) | ENAB in A1 (ml) | ENAB in A2 (ml) | Ti (% wt) | Mg (% wt) | EtO (% wt) | ENAB (% wt) |
|---|---|---|---|---|---|---|---|---|---|---|
| 8 | 115 | 115 | 115 | .09 | 1.0 | 1.0 | 4.1 | 18.3 | 0.28 | 7.75 |
| 9 | 115 | 115 | 115 | 1.2 | 1.1 | 1.1 | 3.9 | 17.2 | 0.28 | 7.94 |
| 10 | 105 | 105 | 105 | 1.1 | 1.1 | 1.1 | 3.3 | 17.7 | 0.20 | 14.5 |
| 11 | 110 | 110 | 110 | 1.1 | 1.1 | 1.1 | 4.1 | 18.4 | 0.40 | 7.59 |
| 12 | 105 | 105 | 105 | 0.7 | 0.7 | 0.7 | 3.9 | 18.2 | 0.54 | 12.4 |
| 13 | 110 | 110 | 110 | 0.5 | 0.5 | 0.5 | 4.5 | 17.6 | 0.73 | 10.1 |

ENAB denotes 1-ethoxy-2-n-alkoxybenzene

The data in Table 2 represent average values: the values reported for example 8 were based on the average of 8 samples; the values reported for example 9 were based on the average of 27 samples; the values reported for example 10 were based on the average of 4 samples; the values reported for example 11 were based on the average of 8 samples; the values reported for example 12 were based on the average of 11 samples; and the values reported for example 13 were based on the average of 4 samples.

The data indicate that fairly normal looking procatalysts can be prepared at 105–115° C. using about 0.5–1.5 ml of ENAB in each mixed solvent contact. The titanium values are somewhat elevated in the 3.2–4 range but it would appear that the ethoxide levels can be controlled below 0.5% wt.

The data for 1-ethoxy-2-n-butoxybenzene (example 9) indicate the importance of ENAB addition to each mixed solvent contact. Thermally, the most reliable preparation temperatures were around 110–115° C. as far as reasonable loadings of titanium and electron donor were concerned. It was found that higher temperatures led to elevated titanium values along with reduced incorporation of electron donor. As in the previous example, it would appear as if 1.0 ml of electron donor per mixed solvent contact is about the optimum quantity to employ in order to obtain representative analyses.

The average values for the four procatalysts prepared using 1-ethoxy-2-n-pentoxybenzene as the electron donor are provided in Table 2 as example 10. No temperatures above 110° C. were employed in these experiments and this resulted in a very reproducible set of analytical data. The loading of electron donor increased as the preparation temperature decreased with little meaningful variation in ethoxide content even at 100° C. This particular electron donor provided one of the most reliable procatalysts in terms of reproducibility and desirable analyses.

The average values for the hexoxy, heptoxy, and octoxy ethoxybenzenes are shown in Table 2 as examples 11, 12, and 13, respectively. Similar trends were observed as with the lower chain lengths but somewhat more pronounced. In general, the titanium loadings remained elevated as did the ethoxides. As before, the conditions that led to the most representative analysis were around 110° C. temperature and 1.0 ml of dialkoxybenzene per mixed solvent contact.

Polymerization

Liquid propylene polymerization was conducted in a stirred autoclave in a manner similar to that described above with respect to examples 1–7. DCPDMS was used as the external selectivity control agent. The results of the polymerizations are shown in Table 3 below.

TABLE 3

| Example | Yield (kg/g-cat-hr) | Yield (MMgPP/g-Ti-hr) | XS (% wt) | MF (g/10 min) |
|---|---|---|---|---|
| 8 | 36.8 | 0.90 | 4.2 | 3.6 |
| 9 | 41.0 | 1.05 | 4.7 | 2.6 |
| 10 | 45.1 | 1.34 | 1.5 | 2.0 |
| 11 | 43.4 | 1.08 | 2.3 | 5.0 |
| 12 | 32.3 | 0.84 | 2.7 | 5.4 |
| 13 | 28.6 | 0.41 | 3.4 | 5.6 |

The data reported in Table 3 represent average values: the values reported for example 8 were based on the average of 8 polymerization experiments; the values reported for example 9 were based on the average of 23 polymerization experiments; the values reported for example 10 were based on the average of 4 polymerization experiments; the values reported for example 11 were based on the average of 8 polymerization experiments; the values reported for example 12 were based on the average of 11 polymerization experiments; and the values reported for example 13 were based on the average of 3 polymerization experiments.

The 1-ethoxy-2-n-alkoxybenzene electron donors provide catalysts that have superior activity and a lower xylene solubles content when compared to veratrole, and when compared to other dialkoxybenzene electron donors.

EXAMPLES 14, 15, AND COMPARATIVE D

Figure 3:
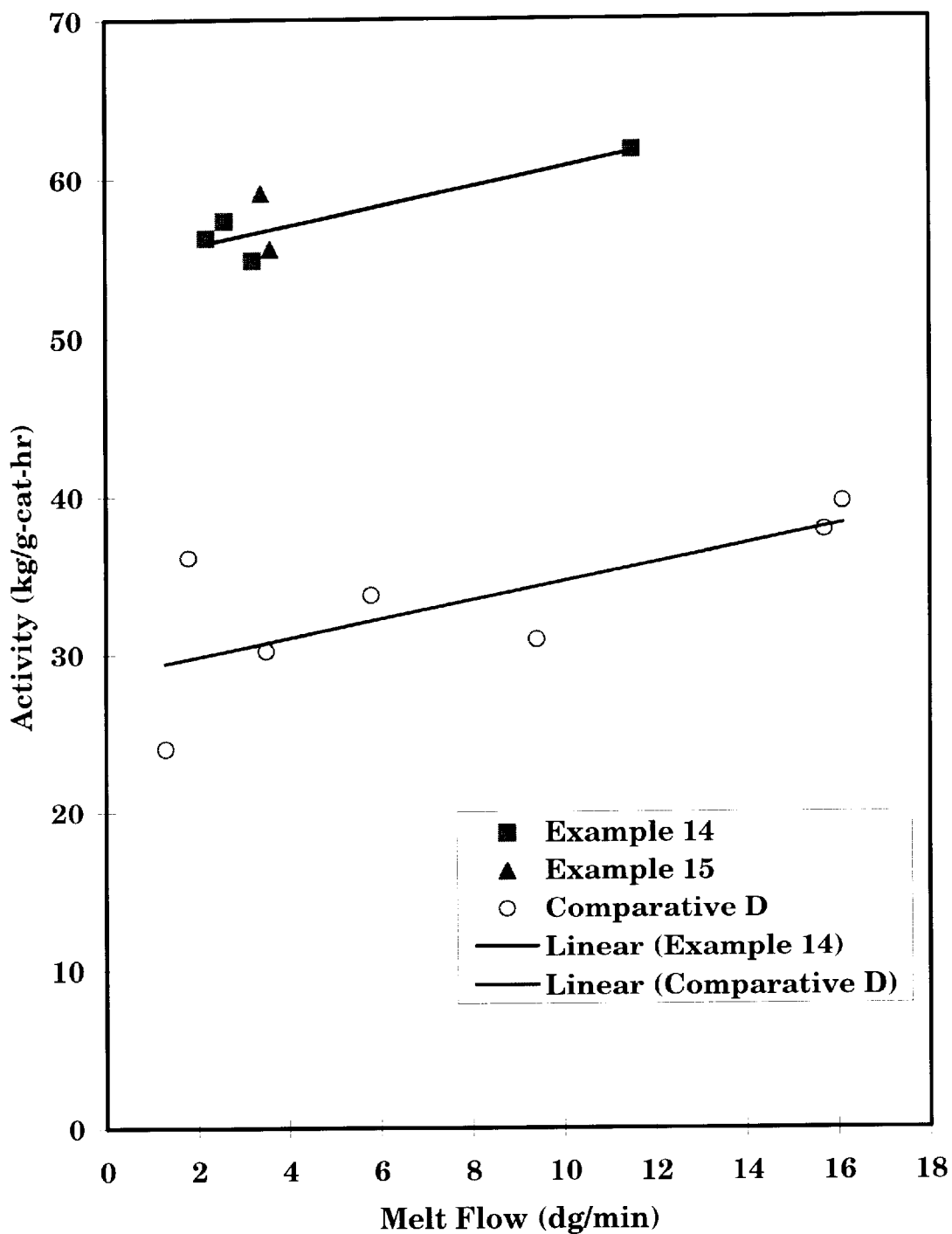
FIG. 3 is a graphical representation of the results obtained from examples 14, 15, and comparative D.

Several procatalysts were prepared using the methods described above with reference to examples 8–13. The internal electron donor for inventive examples 14 and 15 were 1-ethoxy-2-n-pentoxybenzene and the procatalysts were prepared under close to optimum conditions for best polymerization performance. Comparative example D was procatalyst prepared in a manner similar to that described in U.S. Pat. No. 5,093,415 using a conventional electron donor, diisobutyl phthalate. Each of the catalysts was used in a liquid propylene stirred polymerization in a manner similar to that described above with reference to examples 8–13 with the exceptions that 0.17 mmol DCPDMS, 0.005 mmol Ti, and varying hydrogen concentrations were used. Hydrogen concentrations were varied to control MF. The results are shown in Table 4 below and in FIG. 3. These results are similar to the results that were obtained with procatalysts using of the electron donors of the present invention that were prepared under close to optimum conditions for best polymerization performance.

TABLE 4

| Catalyst | MF (g/10 min) | Yield (kg/g precursor) | XS % wt |
|---|---|---|---|
| 14 | 2.2 | 56.3 | 2.5 |
| 14 | 2.6 | 57.4 | 1.3 |
| 14 | 3.2 | 54.9 | 1.5 |
| 14 | 11.5 | 61.8 | 1.8 |
| 15 | 3.4 | 59.1 | 2.7 |
| 15 | 3.6 | 55.6 | 1.5 |
| D | 1.3 | 24.0 | 1.0 |
| D | 1.8 | 36.1 | 1.6 |
| D | 3.5 | 30.2 | 1.1 |
| D | 5.8 | 33.7 | 1.3 |
| D | 9.4 | 30.9 | 1.6 |
| D | 15.7 | 37.8 | 1.1 |
| D | 16.1 | 39.6 | 1.3 |

As can be seen from Table 4, the use of the electron donors of the present invention provides selectivity as measured by xylene soluble content that is comparable to a conventional electron donor, diisobutyl phthalate. The data in the above table was plotted in FIG. 3 to show the relationship between melt flow (in g/10 min) and yield (i.e., activity). As can be seen from FIG. 3, the use of the electron donors of the present invention provides superior yield, when compared to a conventional electron donor, diisobutyl phthalate.

While the invention has been described in detail with reference to particularly preferred embodiments and examples, those skilled in the art will appreciate that various modifications may be made to the invention without departing from the spirit and scope thereof.

We claim:

1. A method of polymerizing at least one olefin comprising contacting the at least one olefin with a catalyst composition comprising:

1) a procatalyst composition comprising a magnesium and titanium-containing component and an electron donor compound of the structure:

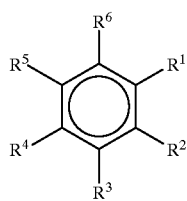

(I)

wherein $R^1$ is ethoxy, $R^2$ is $C_{1-10}$ alkoxy, and $R^3$–$R^6$ are each individually, hydrogen, hydrocarbyl, hydrocarboxyl, nitro, silyl or halo;

2) a co-catalyst, and optionally 3) a selectivity control agent.

2. A method according to claim 1, wherein $R^2$ is selected from the group consisting of n-propoxy, n-butoxy, n-pentoxy, n-hexoxy, n-heptoxy, and n-octoxy.

3. A method according to claim 1, wherein $R^3$, $R^5$ and $R^6$ are hydrogen.

4. A method according to claim 1, wherein $R^3$, $R^4$, $R^5$, and $R^6$ are hydrogen.

5. A method according to claim 1, wherein the electron donor compound is selected from the group consisting of: 1-ethoxy-2-n-propoxybenzene; 1-ethoxy-2-n-butoxybenzene; 1-ethoxy-2-n-pentoxybenzene; 1-ethoxy-2-n-hexoxybenzene, 1-ethoxy-2-n-heptoxybenzene, and 1-ethoxy-2-n-octoxybenzene.

6. A method according to claim 1 wherein the procatalyst comprises the reaction product of:

a. a magnesium source; and b. $Ti(OR')_nX_{4-n}$ wherein n is from 0 to 2, X is a halide and R' is a hydrocarbon.

7. A method according to claim 6, wherein the procatalyst forming reaction takes place in the presence of a halohydrocarbon.

8. A method according to claim 6, wherein component (b) is $TiCl_4$.

9. A method according to claim 6, wherein the magnesium source is selected from the group consisting of a magnesium alkyl, magnesium aryl, magnesium alkaryl, magnesium halide, magnesium alkoxide, magnesium alkaryloxide, and magnesium aryloxide compounds, and carbonated complexes thereof.

10. The method of claim 1 wherein $R^2$ is $C_{2-10}$ alkoxy.

11. The method of claim 1 wherein $R^2$ is $C_{3-10}$ alkoxy.

12. The method of claim 1 wherein the olefin is selected from the group consisting of ethylene and alpha-olefins of from 3 to 10 carbons.

13. The method of claim 1 wherein ethylene, propylene, or a mixture thereof is polymerized.

* * * * *